United States Patent [19]
Murphy

[11] Patent Number: 5,328,577
[45] Date of Patent: * Jul. 12, 1994

[54] UPGRADING OF LOW VALUE HYDROCARBONS USING A HYDROGEN DONOR AND MICROWAVE RADIATION

[75] Inventor: William J. Murphy, Brights Grove, Canada

[73] Assignee: Exxon Research & Engineering Co., Florham Park, N.J.

[*] Notice: The portion of the term of this patent subsequent to Dec. 4, 2007 has been disclaimed.

[21] Appl. No.: 985,782

[22] Filed: Dec. 4, 1992

Related U.S. Application Data

[63] Continuation-in-part of Ser. No. 457,603, Dec. 27, 1989, Pat. No. 5,181,998.

[51] Int. Cl.⁵ ................................ C07C 4/00
[52] U.S. Cl. ........................ 204/168; 204/157.43; 204/157.47; 204/170
[58] Field of Search ............... 204/157.43, 157.47, 204/157.6, 168, 170

[56] References Cited

U.S. PATENT DOCUMENTS

| | | | |
|---|---|---|---|
| 3,328,276 | 6/1967 | Schmidt et al. | 204/170 |
| 3,663,394 | 5/1972 | Kawahara | 204/168 |
| 4,234,402 | 11/1980 | Kirkbride | 204/162 |
| 4,279,722 | 7/1981 | Kirkbride | 204/162 |
| 4,474,625 | 10/1984 | Cohen et al. | 148/1.5 |
| 4,574,038 | 3/1986 | Wan | 204/162 |
| 4,721,828 | 1/1988 | Withers | 585/500 |
| 4,919,974 | 4/1990 | McCune et al. | 427/249 |
| 4,975,164 | 12/1990 | Ravella et al. | 204/157.43 |
| 5,015,349 | 5/1991 | Suib et al. | 204/168 |
| 5,181,998 | 1/1993 | Murphy et al. | 204/170 |

OTHER PUBLICATIONS

Hawley's *Condensed Chemical Dictionary*, Sax and Lewis, Sr., New York, p. 1232.

Gasner et al., "Microwave and conventional pyrolysis of a bituminous coal", Chemical Abstracts 106: 7281h (1987).

Tanaka et al., "A Stoicheiometric Conversion of $CO_2+CH_4$ into $2\ CO+2\ H_2$ by Microwave Discharge", J. Chem. Soc., Chem. Commun., pp. 921-922 (1982).

*Primary Examiner*—John Niebling
*Assistant Examiner*—Cybille Delacroix-Muirheid
*Attorney, Agent, or Firm*—James H. Takemoto

[57] ABSTRACT

Low value hydrocarbons can be upgraded by contact with the products formed during irradiation of a hydrogen donor and water using microwave energy in the presence of at least one plasma initiator.

10 Claims, 3 Drawing Sheets

UPGRADING OF LOW VALUE HYDROCARBONS USING A HYDROGEN DONOR AND MICROWAVE RADIATION

This application is a continuation-in-part of U.S. Ser. No. 457,603, now U.S. Pat. No. 5,181,998, filed Dec. 27, 1989.

BACKGROUND OF INVENTION

1. Field of the Invention

This invention relates to a method for upgrading a low value hydrocarbon by contact with the products formed during cracking of a hydrogen donor in the presence of water using microwave radiation.

2. Description of Related Art

Microwave energy has been used to convert methane to other hydrocarbons. For example, U.S. Pat. No. 4,574,038 discloses that methane can be converted to ethylene and hydrogen in a batch process at pressures of from 0.3 to 1 atmosphere by subjecting the methane to microwave radiation in the presence of a metal powder catalyst. Another example of methane conversion using microwave energy is U.S. Pat. No. 3,663,394.

Microwave energy has been used to treat liquid hydrocarbons. For example, U.S. Pat. No. 3,616,375 discloses a method of decreasing the sulfur content of crude oil and other petroleum products using microwave energy. As another example, U.S. Pat. No. 4,234,402 discloses that a variety of petroleum products can be hydrogenated and desulfurized by contact with hydrogen and microwave energy. As yet another example, U.S. Pat. No. 4,279,722 discloses that a number of petroleum refinery operations can be improved by subjecting the hydrocarbon reactants and catalysts to microwave energy. German Patent 2,535,119 discloses a method for conducting chemical reactions by subjecting a catalyst particle in a fluid medium containing the chemical reagents to microwave energy. In addition, U.S. Pat. No. 4,975,164 discloses the conversion of $C_{2+}$ hydrocarbons to primarily unsaturated hydrocarbons and hydrogen using microwave radiation.

However, none of these patents suggest the particular upgrading process described below.

SUMMARY OF THE INVENTION

This invention concerns a method for upgrading a low value hydrocarbon which comprises:
 (a) introducing into a reaction zone containing at least one plasma initiator capable of initiating an electric discharge in an electromagnetic field, a feed stream wherein said feed stream contains
  (1) a hydrogen donor with the proviso that if the hydrogen donor is not molecular hydrogen, then molecular hydrogen is added in an amount sufficient to maintain activity of the plasma initiator,
  (2) from about 0.02 to about 20 wt% water, based on the feed stream, and
  (3) low value hydrocarbon;
 (b) subjecting the reaction zone to microwave radiation having a frequency of at least 0.3 GHz thereby initiating an electric discharge; and
 (c) cracking the hydrogen donor in the presence of the electric discharge thereby upgrading at least a portion of the low value hydrocarbon.

DETAILED DESCRIPTION OF THE INVENTION

Figure 1:
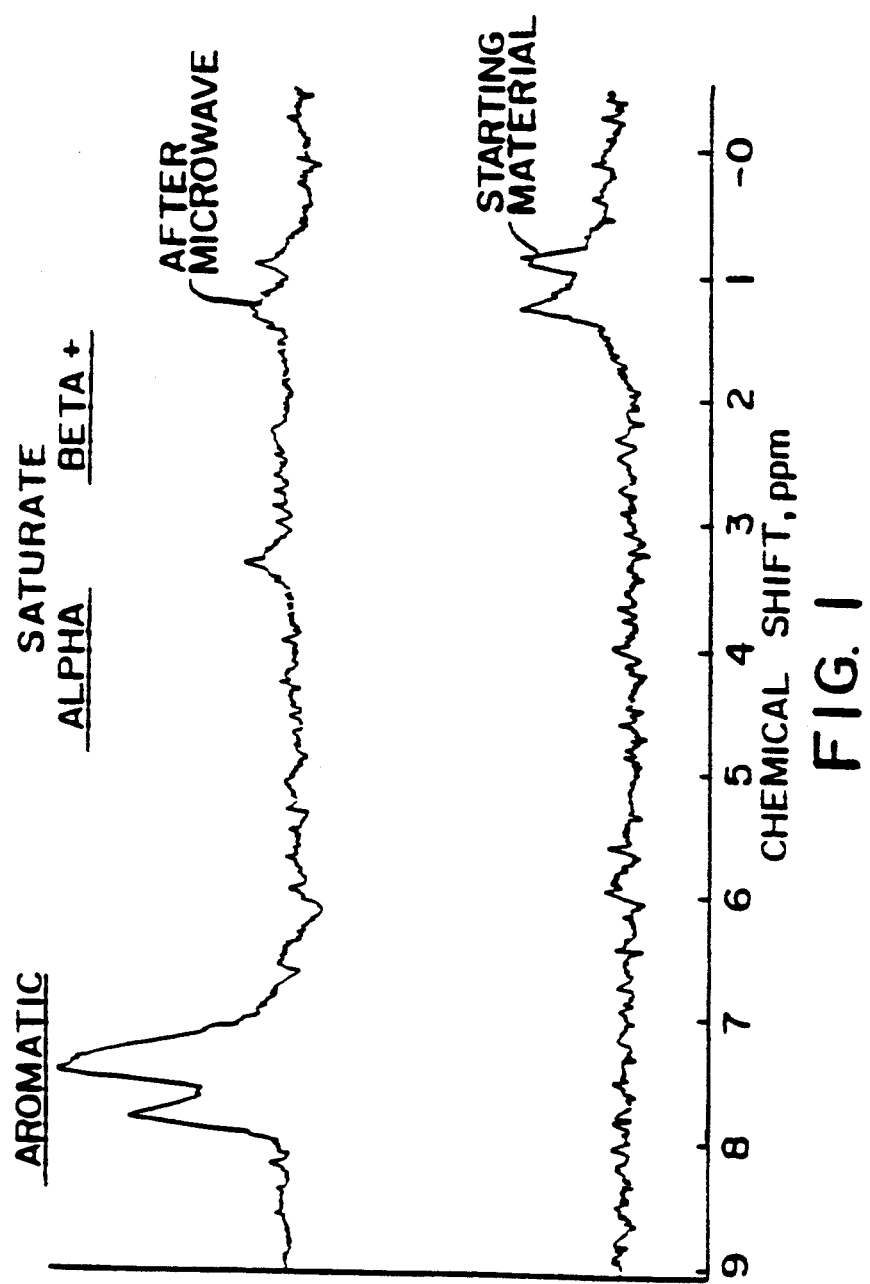
FIG. 1 shows the deuterium NMR spectra of Cold Lake crude before and after irradiation with microwave energy.

This invention requires the presence of a low value hydrocarbon, a hydrogen donor, water, at least one plasma initiator, and a microwave source. A feed stream containing hydrogen donor, water and low value hydrocarbon is subjected to microwave radiation in a reaction zone containing at least one plasma initiator. The plasma initiator(s) generate an electrical discharge which causes the hydrogen donor to crack, i.e., thermally dissociate into reactive species. The identity of the reactive species is not precisely known although they are likely radicals which react with the low value hydrocarbons.

By initiating cracking of the hydrogen donor in the presence of water, it has been discovered that the energy efficiency or rate of dissociation of the hydrogen donor is substantially increased thereby improving the efficiency of the overall upgrading process. The amount of water necessary to enhance the upgrading process ranges from about 0.02 to about 20 wt% based on feed, preferably about 0.1 to about 5 wt%.

Essentially any low value hydrocarbon can be upgraded according to this invention. As used herein, "low value hydrocarbon" or "low value hydrocarbons" refers to any carbonaceous material (synthetic or naturally occurring) of low commercial value that can be upgraded to a product of greater commercial value. For example, this could include upgrading a hydrogen deficient hydrocarbon to a hydrocarbon that is more hydrogen rich, upgrading a low octane (or low cetane) hydrocarbon to a hydrocarbon having a higher octane (or cetane) number, reducing the level of contaminants (e.g. sulfur, nitrogen, aromatics, metals, PNAs, etc.) in a hydrocarbon to improve the quality (e.g. viscosity index, octane, cetane, pour point, luminosity, smoke point, etc.) of the hydrocarbon, and the like. Suitable low value hydrocarbons include whole crude as well as any of its fractions such as naphthas, light gas oils, heavy gas oils, residual fractions, reduced crude oils, cycle oils derived from any of these, or mixtures thereof. The low value hydrocarbon may be derived from petroleum sources or from shale oil kerogen, tar sands, bitumen processing, synthetic oils, coal hydrogenation, and the like. The low value hydrocarbon may be in the gas (or vapor) phase or in the liquid phase at upgrading conditions.

The term "hydrogen donor" refers to any chemical species having donatable hydrogen. This includes a wide variety of hydrocarbons and non-hydrocarbons. Examples include $H_2$, $H_2S$, $CH_4$, $C_2H_6$, $C_3H_8$, cyclohexane, dimethyl sulfide, xylene, etc., or mixtures thereof. Other gases such as $N_2$ may be present as well. Methane, hydrogen, or mixtures thereof are preferred hydrogen donors.

The term "upgrading" is meant to include a variety of processes such alkylation, cracking, demetalization, denitrogenation, desulfurization, hydrocracking, hydrogenation, isomerization, pour point reduction, combinations thereof, and the like. However, the particular type of upgrading obtained will depend on the particular low value hydrocarbon used, the operating conditions (and procedures) employed, and the particular donor used. For example, should hydrogen atoms dominate the product mix then hydrogenation would be expected to be the dominant upgrading step. However, if alkyl radicals or ions are the dominant active species, then alkylation would be the dominant reaction. Suitable hydrocarbon feedstocks for the above mentioned upgrading processes are well known in the art.

The hydrogen donor should always be in intimate contact with the plasma initiators. In addition, the degree of contact between the low value hydrocarbon and the plasma initiators will affect the product slate. Maximizing the low value hydrocarbon/plasma initiator contact (for example, by maintaining the low value hydrocarbon in the vapor phase or as a mist) would be expected to enhance conversion (e.g. cracking, hydrocracking, etc.) and skeletal rearrangement (e.g. isomerization, reforming, etc.). However, should contact between the initiators and the low value hydrocarbon be minimized (for example, by maintaining more of the low value hydrocarbon in the liquid phase), then processes such as alkylation, demetalization, denitrogenation, desulfurization, hydrogenation, etc. would be favored. The upgrading reactions of this invention will occur only if the low value hydrocarbon is in intimate contact with the short-lived dissociation products (e.g. radicals or ions) from the hydrogen donor.

The plasma initiator may be essentially any material capable of accumulating an electric charge when placed in an electromagnetic field and then dissipating the charge (or initiating an electric discharge), for example, by ionizing a gas environment. This includes metal initiators, non-metal initiators (including semiconductors), and composites of metal and non-metal initiators. As used herein, "composite" is meant to include mixtures (or combinations) of metals and non-metals. Examples of suitable metal initiators are tungsten, iron, nickel, copper, their alloys, or mixtures thereof. Preferred metal initiators are tungsten, iron, or mixtures thereof. Examples of suitable non-metal initiators include carbon, alumina, manganese dioxide, magnetite, nickel oxide (e.g. NiO), iron oxide (e.g. $Fe_3O_4$), calcium aluminate, cobalt oxide, chromium nitride, iron sulfide (e.g. $FeS_2$, $Fe_{1-x}S$) copper sulfide (e.g. $Cu_2S$) or mixtures thereof. Carbon, iron oxide, and calcium aluminate are preferred, with carbon being particularly preferred. Silica is not a suitable non-metal initiator. However, silica composited with a metal initiator or another non-metal initiator would be a suitable plasma initiator.

Although upgrading can be effected using only one plasma initiator, upgrading is enhanced if more than one (e.g. 6 or more) plasma initiators is used. Preferably, a plurality of plasma initiators are used. Most preferably, the plasma initiator will comprise a plurality of metal wire segments. Each plasma initiator should be of at least a minimum length that is sufficient to initiate an electric discharge when placed in an electromagnetic field. However, the precise minimum length of each initiator will vary with the frequency of the microwave source as well as the geometry of the reaction zone and of the initiator.

If more than one plasma initiator is used, a minimum distance should be maintained between each initiator to facilitate dissipation of the electric charge. However, the minimum distance will vary depending upon the frequency of the microwave source. As an example, the minimum distance should be at least about 0.25 cm, preferably at least about 0.5 cm, for a frequency of 2.45 GHz.

The plasma initiators should be elongated, but may be formed, combined, or bent in any convenient shape (e.g. straight, helix, spiral, and the like). Preferably, the initiators should be formed such that there are points or sharp edges at the ends or on the surface of the initiators.

The plasma initiators may be stationary within the reaction zone or they may be in motion. The motion can result from the initiators being fluidized by a gas (e.g. the hydrogen donor) or by other means (e.g. an external magnetic field gradient).

The frequency of the microwave source can vary broadly. Typically, however, the microwave energy will have a frequency of at least 0.3 GHz, with frequencies centered around 0.915, 2.45, 5.80, or 22.0 GHz being presently preferred in North America; particularly frequencies centered around 0.915, 2.45, or 5.80 GHz; especially frequencies centered around 0.915 or 2.45 GHz.

The microwave energy used in this invention may be continuous or pulsed. If pulsed, the duration of on-time pulses can vary broadly, but typically will range from about 1 nanosecond to about 20 seconds, preferably from about 1 millisecond to about 10 seconds, and most preferably from about 0.01 to about 0.2 seconds. The duration of off-time rests can vary broadly as well, but typically will range from about 1 nanosecond to about 100 seconds, preferably from about 0.003 to about 60 seconds, and most preferably from about 0.03 to about 5 seconds.

If the hydrogen donor is not molecular hydrogen, then molecular hydrogen should also be present in the reaction zone to maintain the activity of the plasma initiators for upgrading. The amount of hydrogen in the reaction zone during upgrading should be sufficient to maintain a carbon (based on carbon in the molecules in contact with the plasma initiators) to hydrogen weight ratio less than 6:1, preferably less than 4:1, more preferably less than 3:1, and most preferably less than 1.5:1. Although some upgrading may occur at weight ratios of 6:1 or more, greater upgrading will be obtained at lower weight ratios because hydrogen tends to reduce or inhibit the formation of carbonaceous deposits, sulfur deposits, or both on the plasma initiators. While not wishing to be bound by any particular theory, it is believed that at higher weight ratios, greater amounts of deposits accumulate on the initiators and inhibit their ability to ionize the gas environment.

Although extraneous molecular hydrogen need not be added, if a sufficient amount of hydrogen is not present initially in the reaction zone, the initiators will deactivate until a sufficient amount of hydrogen is present (or has accumulated, for example, by recycling hydrogen formed during upgrading) to retard deactivation and maintain the weight ratio at a level that will stabilize the upgrading at a particular level. This so-called induction period results in an initial loss of initiator activity and, hence, a lower level of upgrading than if hydrogen had been present initially. Therefore, to avoid these undesirable results, it is preferred to add extraneous hydrogen to the reaction zone initially to minimize or prevent the initial loss of initiator activity and upgrading capability. This extraneous hydrogen may be pure or in a mixture with other gases (e.g. as from a naphtha reformer) and may be added to the reaction zone separately or in mixture with the low value hydrocarbon.

The upgrading process of this invention can be practiced at any convenient temperature, including ambient conditions. The subject process has the advantage that pressures of one atmosphere or greater can be employed. Pressures of from about 10 torr to about 15 atm preferably about 1 to about 2 atm are suitable.

This invention will be further understood by reference to the following Examples which are not intended to restrict the scope of the appended claims.

EXAMPLE 1

Conversion of Methane Using Continuous Wave Microwave Radiation

A methane/hydrogen mixture (1:4 mole ratio) flowing at 75 ml/min (milliliters/minute) at atmospheric pressure was contacted with 0.37 g of a straight tungsten wire (approximately 0.76 mm in diameter and cut into about 47 mm lengths) in a reactor fabricated from a straight piece of quartz tubing, 7 mm in internal diameter. The part of the tube containing the wire was inserted in a WR430 microwave waveguide and positioned approximately one-quarter wavelength from a short circuit plate. The reactor was then irradiated with continuous microwave radiation centered at a 2.45 GHz frequency, with an average power of 10.0 watts. The methane conversion was calculated to be 4.8% using the following equation:

$$\% \text{ Methane Conversion} = \left[1 - \frac{\text{wt \% methane in the products}}{\text{wt \% methane in the feed}}\right] \times 100$$

After about 30 minutes the primary hydrocarbon products formed were acetylene (an average of 0.89 wt%), and ethylene (an average of 0.68 wt%). The product stream also contained hydrogen (an average of 34.6 wt% versus 33.3 wt% in the mixture fed to the reactor), and small amounts of other higher hydrocarbons. The product stream contained methane (an average of 63.5 wt% versus 66.7 wt% in the mixture fed to the reactor).

EXAMPLE 2

Effect of Water on the Conversion of Methane Using Continuous Wave Microwave Radiation A methane/hydrogen mixture (1:4 mole ratio) containing 1.2 wt% water and having a flow rate of 75 ml/min (milliliters/minute) at atmospheric pressure was contacted with 0.37 g of a straight tungsten wire (approximately 0.76 mm in diameter and cut into about 47 mm lengths) in a reactor as described in Example 1. The reactor was then irradiated with continuous microwave radiation centered at a 2.45 GHz frequency, with an average power of 9.8 watts. The methane conversion was be 10.5%.

After about 30 minutes the primary hydrocarbon products formed were acetylene (an average of 2.17 wt%), and ethylene (an average of 1.8 wt%). The product stream also contained carbon monoxide (an average of 0.18 wt%) and water (an average of 1.1 wt% versus 1.2 wt% in the mixture fed to the reactor) in addition to hydrogen (an average of 34.8 wt%) versus 32.9 wt% in the mixture fed to the reactor), and small amounts of other higher hydrocarbons. The product stream contained methane (an average of 59.0 wt% versus 66.7 wt% in the mixture fed to the reactor).

In comparing Examples 1 and 2, adding water to the methane/ hydrogen reaction mixture results in about a 120% increase in methane conversion under continuous microwave radiation conditions. The methane conversion process generates reactive species which can react to form hydrocarbon products. However, as demonstrated by Examples 5 to 8, if reactive low value hydrocarbons are present, upgrading occurs. Increasing the amount of reactive species generated will improve the upgrading process.

EXAMPLE 3

Conversion of Methane Using Pulsed Microwave Radiation

A methane/hydrogen mixture (1:4 mole ratio) flowing at 75 ml/min (milliliters/minute) at atmospheric pressure was contacted with 0.37 g of a straight tungsten wire (approximately 0.76 mm in diameter and cut into about 47 mm lengths) in a reactor fabricated from a straight piece of quartz tubing, 7 mm in internal diameter. The part of the tube containing the wire was inserted in a WR430 microwave waveguide and positioned approximately one-quarter wavelength from a short circuit plate. The reactor was then irradiated with microwave radiation centered at a 2.45 GHz frequency and pulsed in an on/off cycle (0.07 seconds on in a total of 0.73 seconds) with an average power of 10.2 watts. The methane conversion was 12.6%.

After about 30 minutes the primary hydrocarbon products formed were acetylene (an average of 4.71 wt%), and ethylene (an average of 0.97 wt%). The product stream also contained hydrogen (an average of 35.7 wt% versus 33.1 wt% in the mixture fed to the reactor), and small amounts of other higher hydrocarbons. The product stream contained methane (an average of 58.5 wt% versus 66.9 wt% in the mixture fed to the reactor).

EXAMPLE 4

Effect of Water on the Conversion of Methane Using Pulsed Microwave Radiation

A methane/hydrogen mixture (1:4 mole ratio) containing 0.3 wt% water and having a flow rate of 75 ml/min (milliliters/minute) at atmospheric pressure was contacted with 0.37 g of a straight tungsten wire (approximately 0.76 mm in diameter and cut into about 47 mm lengths) in a reactor as described in Example 1. The reactor was then irradiated with microwave radiation centered at a 2.45 GHz frequency and pulsed in an on/off cycle (0.07 seconds on in a total of 0.73 seconds) with an average power of 9.5 watts. The methane conversion was be 57.1%.

After about 30 minutes the primary hydrocarbon products formed were acetylene (an average of 23.98 wt%) and ethylene (an average of 4.42 wt%). The product stream also contained carbon monoxide (an average of 0.17 wt%) and water (an average of 0.17 wt% versus 0.3 wt% in the mixture fed to the reactor) in addition to hydrogen (an average of 42.3 wt% versus 33.0 wt% in the mixture fed to the reactor), and small amounts of other higher hydrocarbons. The product stream contained methane (an average of 28.6 wt% versus 66.7 wt% in the mixture fed to the reactor).

In comparing Examples 3 and 4, adding water to the methane/ hydrogen reaction mixture results in about a 450% increase in methane conversion under pulsed microwave radiation conditions. As noted previously for Examples 1 and 2, the reactive species generated in the methane conversion process are available for upgrading low value hydrocarbons, and increasing the generation of reactive species will improve the upgrading process.

EXAMPLE 5

Hydrogenation of Cold Lake Crude

A methane/hydrogen mixture (the hydrogen donor) in a 1:4 mole ratio (equivalent to a 1.5:1 carbon to hydrogen weight ratio) flowing at 25 ml/min (milliliters/min) at atmospheric pressure was contacted with 1.5 gm of tungsten wire (0.03 inches in diameter and cut into 45 mm lengths) in a reactor fabricated from WR430 waveguide bounded by quartz plate glass windows and positioned approximately one-quarter waveguide wavelength from a short circuit plate. The reactor also contained a dish containing about 3g of Cold Lake crude [the low value (hydrogen deficient) hydrocarbon], which was separated from the tungsten wire segments by about 2 cm.

The reactor was then irradiated with microwave radiation centered at a 2.45 GHz frequency and pulsed in an on/off cycle (0.14 seconds on in a total of 3.5 seconds) with an average power of 5 watts.

The hydrogen was replaced by deuterium to facilitate analyses of the Cold Lake crude product; i.e., to distinguish incorporation of hydrogen from the gas phase into the Cold Lake crude oil from hydrogen naturally present in the oil. The duration of this experiment was 2 hours. The deuterium NMR spectra of the crude before and after contact with the reaction products of the methane/deuterium methane conversion are shown in FIG. 1. The reaction products as monitored by gas chromatography included acetylene, ethylene, and hydrogen.

FIG. 1 shows the hydrogen (deuterium) distribution in the Cold Lake crude before contact with the methane conversion reaction products. However, after contact with reaction products, the hydrogen (deuterium) distribution is changed significantly in the aromatic components and components alpha to aromatics rings. This in turn illustrates that hydrogen/deuterium has reacted with Cold Lake crude.

EXAMPLE 6

Effect of Plasma Initiator on Hydrogenation of Cold Lake Crude

Experiment 5 was repeated without the tungsten wire being present. The resulting hydrocarbon product had essentially the same hydrogen/deuterium ratio as untreated Cold Lake crude. This example shows that a plasma initiator must be present for hydrogenation of the low value hydrocarbon to occur.

EXAMPLE 7

Hydrogenation of Naphthalene

Figure 2:
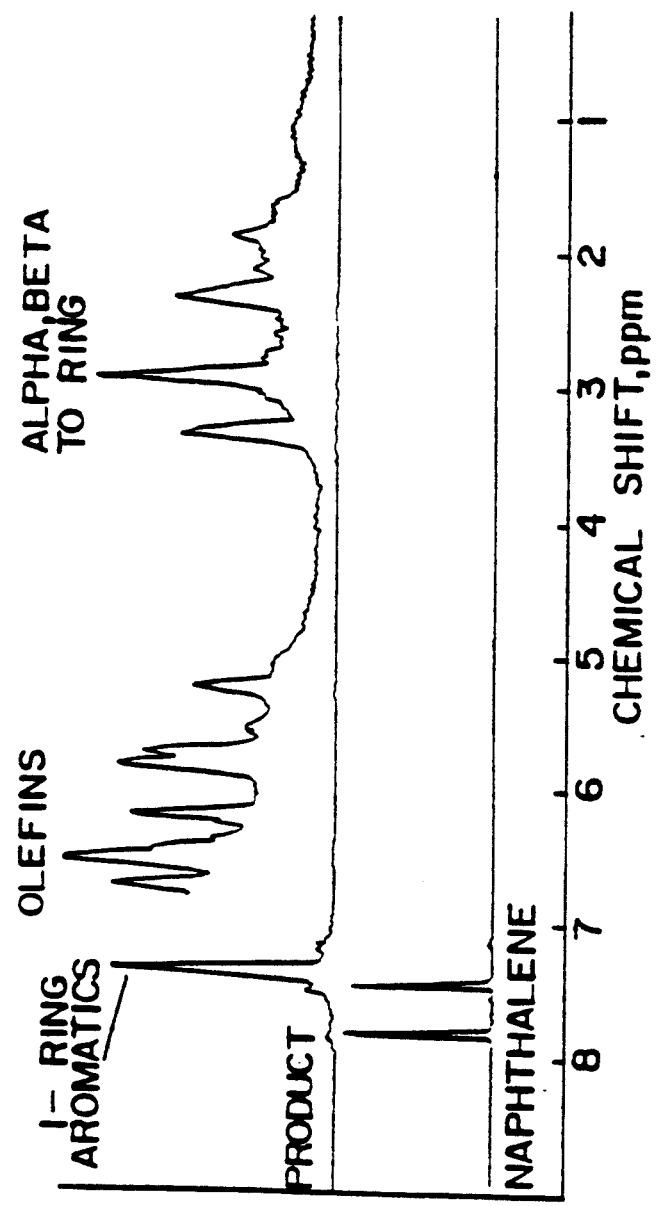
FIG. 2 shows the deuterium NMR spectra of naphthalene before and after irradiation with microwave energy.

Example 5 was repeated using 0.1 g naphthalene instead of Cold Lake crude. The volatile products of this reaction were trapped downstream of the reactor and analyzed by deuterium NMR spectroscopy. The results obtained are shown in FIG. 2. This figure shows that deuterium (or hydrogen) is reacting with the naphthalene, causing hydrogenation of the naphthalene to single ring aromatics.

EXAMPLE 8

Hydrogenation of Naphthalene

Figure 3:
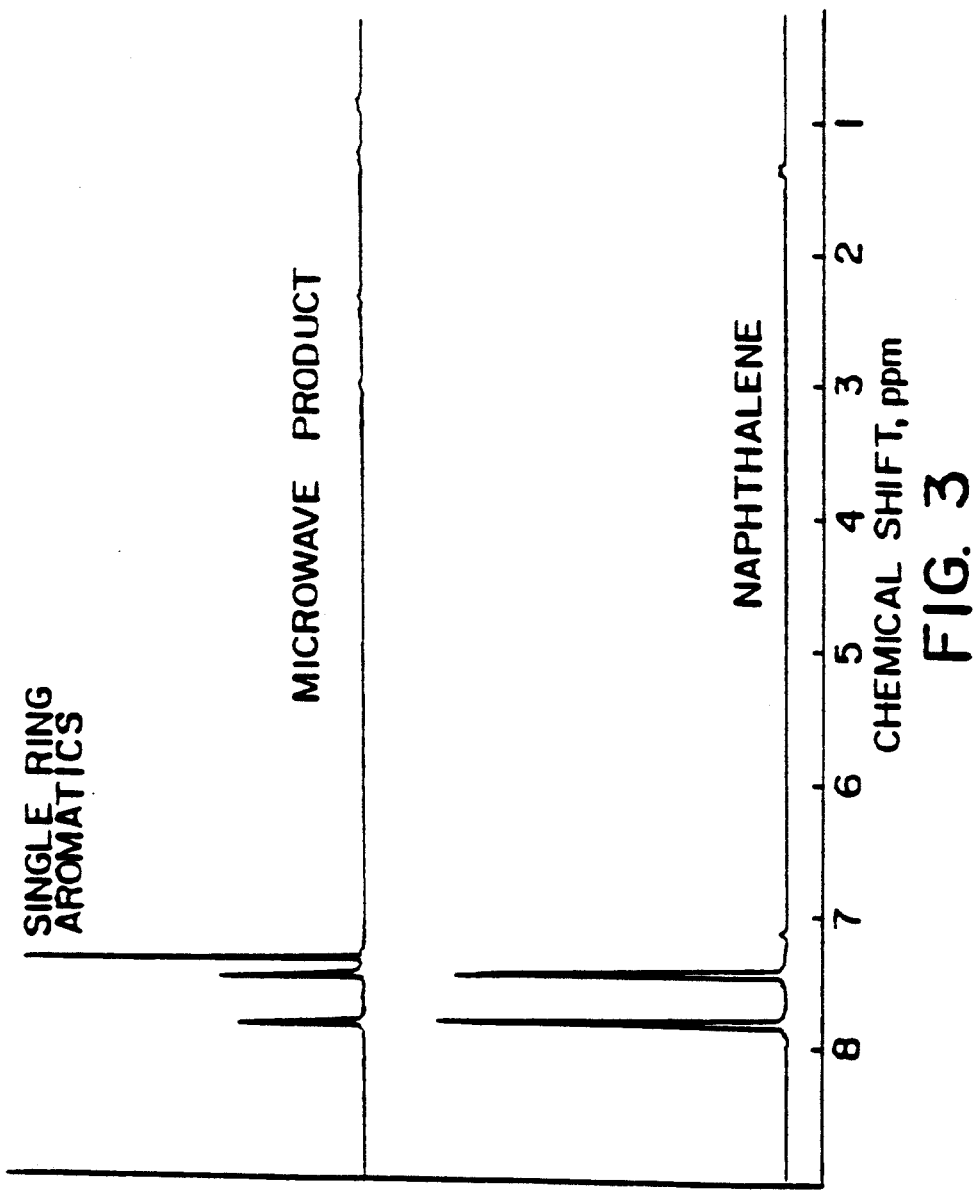
FIG. 3 shows the hydrogen NMR spectra of naphthalene before and after irradiation with microwave energy.

Example 7 was repeated using hydrogen. The hydrogen NMR spectra of the products is illustrated in FIG. 3. This figure shows that naphthalene is being hydrogenated to single ring aromatics.

What is claimed is:

1. A method for upgrading a low value hydrocarbon which comprises:
   (a) introducing into a reaction zone containing at least one plasma initiator capable of initiating an electric discharge in an electromagnetic field a feed stream, wherein said feed stream contains
     (1) a hydrogen donor with the proviso that if the hydrogen donor is not molecular hydrogen, then molecular hydrogen is added in an amount sufficient to maintain activity of the plasma initiator,
     (2) from about 0.02 to about 20 wt% water, based on the feed stream, and
     (3) low value hydrocarbon;
   (b) subjecting the reaction zone to microwave radiation having a frequency of at least 0.3 GHz thereby initiating an electric discharge; and
   (c) cracking the hydrogen donor in the presence of the electric discharge thereby upgrading at least a portion of the low value hydrocarbon.

2. The method of claim 1 wherein the plasma initiator is a metal, a non-metal other than silica or a composite of metal and non-metal.

3. The method of claim 2 wherein the metal is tungsten, iron, nickel, copper, their alloys, or mixtures thereof.

4. The method of claim 2 wherein the non-metal is iron oxide, carbon, calcium aluminate or mixtures thereof.

5. The method of claim 3 wherein the metal is tungsten, iron or mixtures thereof.

6. The method of claim 1 wherein the weight ratio of carbon based on carbon in the molecules in contact with the plasma initiator to hydrogen is less than 6:1 during upgrading.

7. The method of claim 1 wherein a plurality of initiators are present in the reaction zone.

8. The method of claim 1 wherein the amount of water is from about 0.1 to about 5 wt%.

9. The method of claim 1 wherein the feed stream pressure is from about 10 torr to about 15 atm.

10. The method of claim 9 wherein the feed stream pressure is from about 1 to about 2 atm.

* * * * *